United States Patent
Ikami et al.

(10) Patent No.: US 6,458,410 B1
(45) Date of Patent: Oct. 1, 2002

(54) SAMPLE TRAY TO BE USED IN AN IMAGE INFORMATION READER AND FABRICATION METHOD THEREOF

(75) Inventors: Seishi Ikami; Koji Yoshida, both of Kaisei-machi (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 0 days.

(21) Appl. No.: 09/449,904

(22) Filed: Dec. 2, 1999

(30) Foreign Application Priority Data

Dec. 2, 1998 (JP) ............................................ 10-343038

(51) Int. Cl.[7] .............................................. G01N 21/64

(52) U.S. Cl. .................... 427/2.11; 422/82.08; 422/102; 436/172; 436/183

(58) Field of Search ....................... 250/458.1; 356/417, 356/244; 422/162, 82.08, 102, 104, 167; 436/172, 183, 2.11

(56) References Cited

U.S. PATENT DOCUMENTS 6,232,114 B1 * 5/2001 Coassin et al.
6,254,931 B1 * 7/2001 Herpst et al.

* cited by examiner

Primary Examiner—Joseph W. Drodge
Assistant Examiner—Terry K. Cecil
(74) Attorney, Agent, or Firm—Sughrue Mion, PLLC

(57) ABSTRACT

In an image information reader 100 that includes an excitation light source 45, a photoelectric reading mechanism, and an external light shield for reading a sample distributing specific organism-originated material labeled with a fluorescent dye, a sample tray 10 is provided having the qualities of easy rinsing and enduring of repeated use. The sample tray includes a base material, e.g. an aluminum plate 10d, that is coated with a fluororesin, e.g. an hybrid resin 10c of PTFE and PFA having a black color as a base. The tray can also include depressed or projected markings 10a on the surface on which the sample is placed which represent a readable range of the photoelectric reading mechanism. A method of making the sample tray for the reader is also described.

6 Claims, 3 Drawing Sheets

ENLARGED VIEW OF PART B

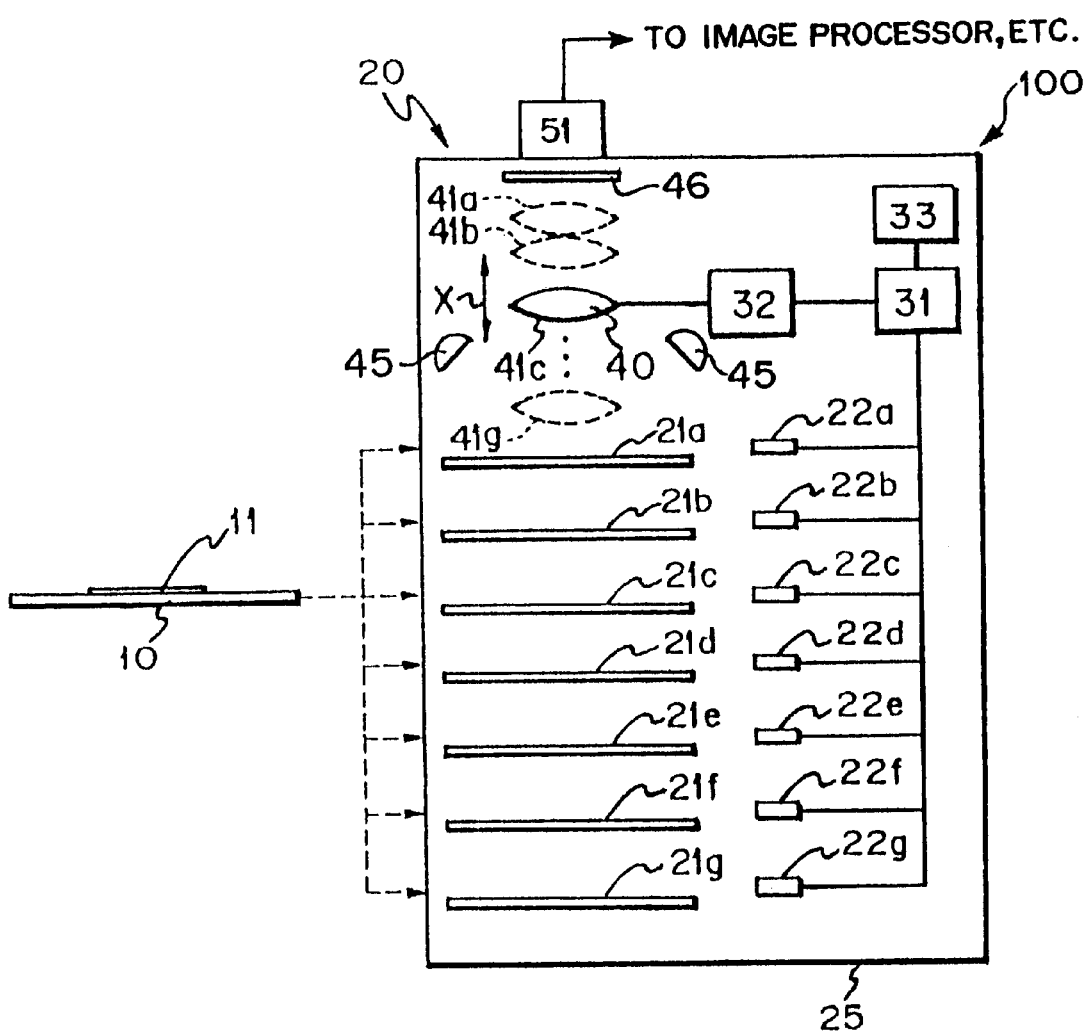

SAMPLE TRAY TO BE USED IN AN IMAGE INFORMATION READER AND FABRICATION METHOD THEREOF

BACKGROUND OF THE INVENTION

1. Field of the Invention

The present invention relates to a sample tray to be used in an image information reader for reading the fluorescent image of a fluorescence-labeled sample and a fabrication method thereof.

2. Description of the Related Art

In the field of biological chemistry and molecular biology, a fluorescence detecting system using a fluorescent dye as a labeling material is hitherto known. According to this system, the evaluations of the arrangement of a gene, the expression level of a gene, the path and state of the metabolism, absorption, and excretion of an applied material in a laboratory mouse, the separation, identification, molecular weight, and characteristics of protein, etc. can be performed, by reading out information about the image of a sample distributing specific organism-originated materials labeled with a fluorescent dye.

For example, using the electrophoresis that causes a living cell in suspension or a biological compound (protein, etc.) in a solution to move to a positive or negative electrode through an electric field by the electric charge, a plurality of DNA fragments are electrophoresed on a gel support body, after a fluorescent dye has been added into a solution containing the plurality of DNA fragments. Alternatively, a plurality of DNA fragments are electrophoresed on a gel support body containing a fluorescent dye, or, after a plurality of DNA fragments have been electrophoresed on a gel support body, this gel support body is immersed into a solution containing a fluorescent dye. In this way, a gel support body (sample) distributing specific DNA fragments (organism-originated materials) labeled with fluorescence is obtained. With external light shielded, the obtained gel support body is irradiated with excitation light for exciting the fluorescent dye employed as a labeling material. The fluorescence emitted from the gel support body is photoelectrically read out. In this way, image information representing a distribution of DNA fragments labeled with fluorescence is acquired, and based on the acquired image information, a visual image is displayed on a display section such as a CRT display, whereby the evaluation of the molecular weight of the DNA fragment and the like can be performed.

Incidentally, in an image information reader to be used in the aforementioned fluorescence detecting system, a sample such as a gel support body is placed on a sample tray. This sample tray usually employs an aluminum sample tray processed with a black Alumite (or Alumilite) so that fluorescence is not erroneously detected.

However, once a fluorescent dye and the like adhere to the aforementioned sample tray, it will take substantial labor to rinse out the fluorescent dye completely. When it cannot be removed to the degree that does not have a bad influence upon fluorescence detection, fluorescence is erroneously detected and therefore the greatest attention must be paid in handling it and sometimes the sample tray cannot be reused.

Hence, a hybrid sample tray superimposing a flat glass pane on an aluminum plate processed with a black Alumite has been made. A sample is placed on the glass pane. However, ghosting is produced due to the reflection from the reverse of the glass pane and noise rises by irregular reflection. There are cases where unfavorable side effects are thus produced.

SUMMARY OF THE INVENTION

The present invention has been made in view of the aforementioned circumstances. Accordingly, it is an object of the present invention to provide a sample tray for an image information reader that is convenient to handle.

The sample tray of the present invention renders rinsing easy and can endure repeated use, by coating the placing surface of the sample tray with fluororesin.

That is, the sample tray according to the present invention is a sample tray on which a sample distributing specific organism-originated materials labeled with a fluorescent dye is placed and which is used in an image information reader having an excitation light source for emitting excitation light and photoelectric reading means for photoelectrically reading out fluorescence emitted from the fluorescent dye exited by the excitation light as a distributed image of the organism-originated materials in the sample and which employs the excitation light source, the sample tray, the sample, and the photoelectric reading means with an external light shield, wherein the sample tray has at least a surface on which the sample is placed coated with fluororesin.

Here, it is preferable that the fluororesin be, for example, a hybrid resin consisting of polytetrafluoroethylene (PTFE) and tetrafluoroethylene-perfluoroalkyl-vinylether copolymer (PFA) with a black color as a base. Specifically, it is preferable to employ Platinum stone (DuPont trademark (hereinafter omitted): Primer; 459-30170, Midocoat; 456-30270, Topcoat; 456-30370) with Silky Black (DuPont trademark (hereinafter omitted)) as a black pigment, 855-100 hybrid resin of PTFE and PFA (DuPont trademark (hereinafter omitted))with 855-023 industrial Primer (DuPont trademark (hereinafter omitted)) as a base, etc. In a conventional sample tray superimposing a glass pane on an aluminum plate processed with a black Alumite, ghosting from the glass pane or irregular reflection is mixed with fluorescence emitted from a sample and detected, so there is a limit in the case where fluorescent image information of high contrast is desired. On the other hand, for hybrid resin of PTFE and PFA with a black color as a base, there is no occurrence of ghosting or irregular reflection, because there is no need to superimpose a glass pane. As a result, fluorescent image information of high contrast can be acquired.

It is desirable for a user's convenience that depressed or projected markings representing a readable range of the photoelectric reading means be formed in the surface of the sample tray of the present invention on which a sample is placed. Particularly, in the case where an image information reader can vary the angle of field, that is, the case where a distance between the photoelectric reading means and the sample tray is variable, markings can be used as a standard when a user disposes a sample within a reading range suitable to a distance between both, if the markings are formed such that they are suitable to each reading range corresponding to each distance between both. The sample tray with markings is thus convenient to use.

Note that the markings formed in a depression or projection formed in a sample tray itself can acquire an image signal more accurately than painted markings. That is, there are cases where some of the paints to be used in marking emit fluorescence in no small amount. When a sample is irradiated with excitation light, in such a case, fluorescence emitted from the markings is mixed with fluorescence emitted from the fluorescent dye contained in the sample, so that the mixture is photoelectrically read out as a noise component. On the other hand, in the markings formed by the depressed or projected configurations of a sample tray itself without employing such paint, there is no occurrence of such local noise and therefore an image signal can be acquired accurately.

As a sample, various forms, such as a gel support body and a membrane filter, a micro-titre plate, and a slide glass transferring this gel thereon, can be employed if specific organism-oriented materials labeled with a fluorescent dye are distributed.

The sample-tray fabricating method according to the present invention is a method of fabricating a sample tray on which a sample distributing specific organism-originated materials labeled with a fluorescent dye is placed and which is used in an image information reader which is equipped with an excitation light source for emitting excitation light and photoelectric reading means for photoelectrically reading out fluorescence emitted from the fluorescent dye by the excitation light as a distributed image of the organism-originated materials in the sample and which employs the excitation light source, the sample tray, the sample, and the photoelectric reading means with external light shield, the method comprising the steps of:

coating at least a surface, on which the sample is placed, with fluororesin; and forming depressed or projected markings, which represent a readable range of the photoelectric reading means, on the surface on which the sample is placed.

Note that it is preferable that the fluororesin be a hybrid resin consisting of polytetrafluoroethylene (PTFE) and tetrafluoroethylene-perfluoroalkyl-vinylether copolymer (PFA).

According to the sample tray of the present invention, the sample-placing surface is coated with fluororesin. Therefore, even if fluorescent dye, a sample, etc. have adhered to the sample-placing surface, these can be rinsed out by simple washing. Thus, the sample tray of the present invention is easy to handle and can sufficiently endure repeated use.

In addition, according to the sample fabricating method of the present invention, depressed or projected markings are formed after the fluororesin has been coated. Therefore, as compared with the case where fluororesin is coated after formation of the markings, the occurrence of unevenness in the fluororesin coat thickness in the marked portions and the vicinities is less likely and therefore there is an advantage of reducing the influence on read image information caused by unevenness in the thickness of the fluororesin coat.

Furthermore, the process of coating fluororesin requires annealing to be performed at 400° C. or so and this annealing process causes a sample tray to deform thermally. For this reason, after the annealing process, there is a need to correct this deformation by plastic deformation. However, since the aforementioned process of forming markings is performed after the coating process, the marking formation process and the thermal-deformation correcting process can be performed collectively. Thus, the number of processes can be reduced, compared with the case where a sample tray is fabricated in the order of the marking process, the coating process, and the correcting process.

BRIEF DESCRIPTION OF THE DRAWINGS

The above and other objects and advantages will become apparent from the following detailed description when read in conjunction with the accompanying drawings, wherein:

FIG. 3 is a sectional view illustrating the essential parts of the image information reader shown in FIG. 2.

DESCRIPTION OF THE PREFERRED EMBODIMENTS

A preferred embodiment of a sample tray of the present invention will hereinafter be described with reference to the drawings.

Figure 1A:
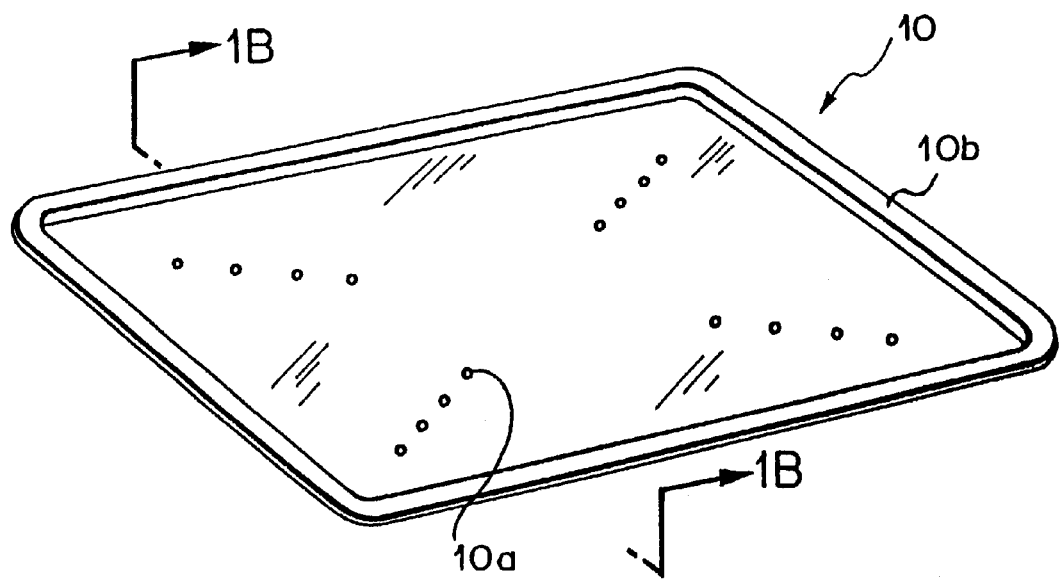
FIG. 1A is a perspective view illustrating a preferred embodiment of a sample tray of the present invention.
Figure 1B:
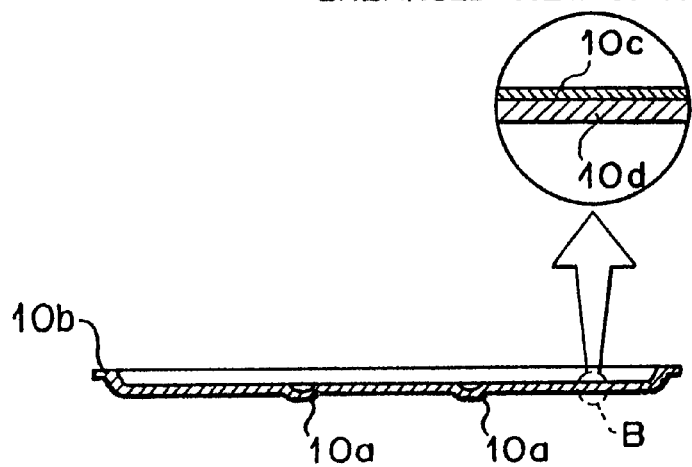
FIG. 1B is a cross sectional view taken along line 1B—1B in FIG. 1A.
Figure 2:
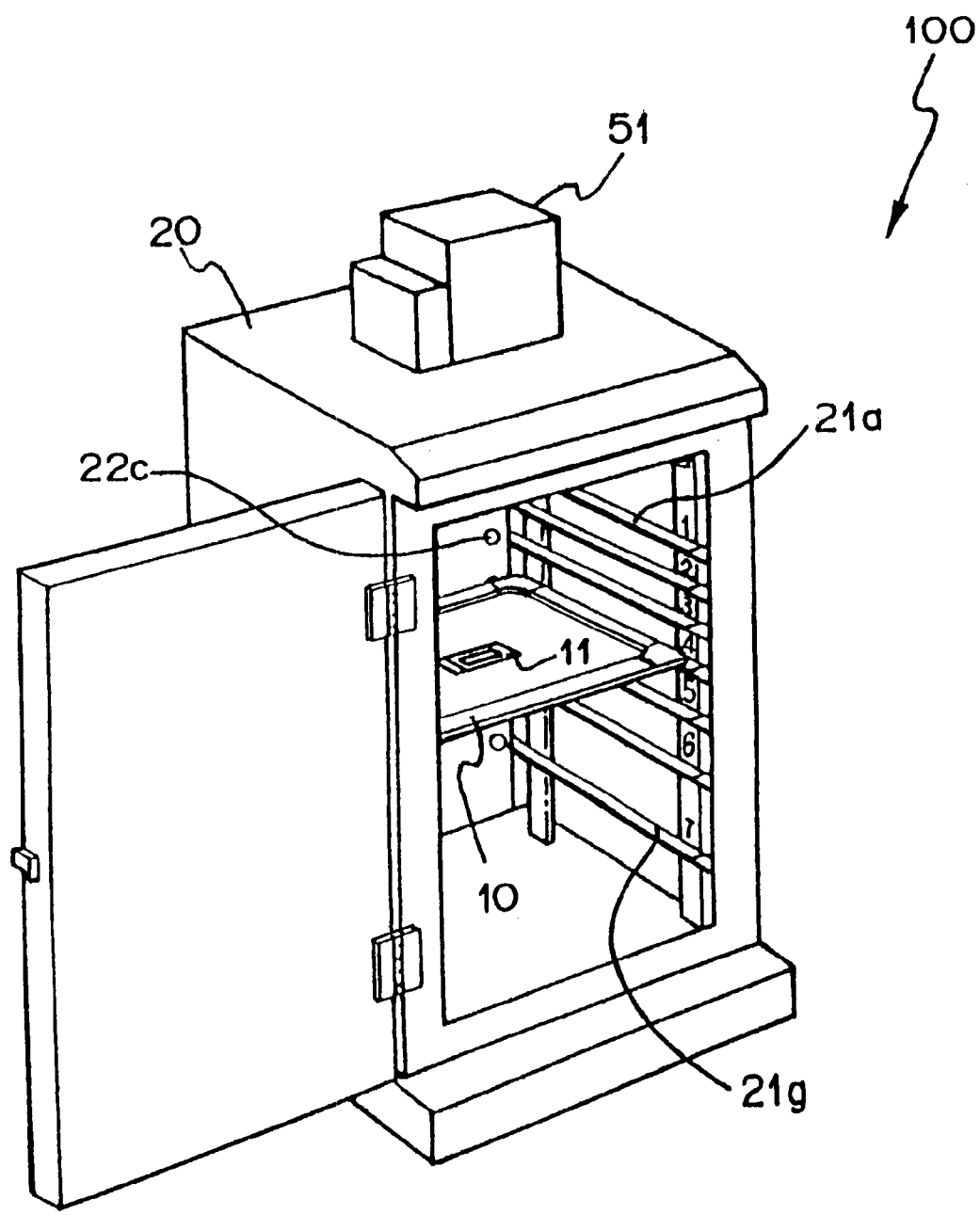
FIG. 2 is a schematic perspective view illustrating an example of an image information reader employing the sample tray shown in FIG. 1.

FIGS. 1A and 1B show the preferred embodiment of the sample tray of the present invention, FIG. 2 shows an example of an image information reader employing the sample tray shown in FIGS. 1A and 1B, and FIG. 3 shows the interior of the image information reader shown in FIG. 2.

In the sample tray 10 illustrated in FIGS. 1A and 1B, an aluminum plate 10d, which is a base material, is coated with hybrid resin 10c consisting of PTFE and PFA with a black color as a base (see FIG. 1B). More specifically, it is coated with Platinum Stone with Silky Black as a black pigment.

Also, the circumferential edge portion of the sample tray 10 rises upward and forms a flange 10b. Furthermore, the flat portion other than the circumferential edge portion is provided with markings 10a indicating the readable range of a charged-coupled device (CCD) 51 that varies according to a location position with respect to an image information reader 100 to be described later, that is, a plurality of ranges, different in size, which hold a sample such as gel. After the aforementioned hybrid resin 10c has been coated, the markings 10a are formed by depressing small circles with respect to the surface on which a sample such as gel is placed. Note that the markings may be formed in projection form with respect to the placing surface. However, since there are cases where a sample strikes the projected markings and inclines, depressed markings are preferred.

On the other hand, the image information reader 100 illustrated in FIGS. 2 and 3 is provided with (1) the sample tray 10 of FIGS. 1A and 1B for holding gel 11 distributing specific organism-originated materials labeled with a fluorescent dye, within a black box 20 whose interior is shielded from light; (2) light-emitting diodes 45 for emitting excitation light to the gel 11 placed on the sample tray 10; (3) an interline-type CCD 51 with cooling elements for photoelectrically detecting florescence emitted from the fluorescent dye in the gel 11 by the excitation light and outputting an obtained image signal to an external image processor; (4) a lens 40 for projecting the image of the gel 11 on the sample tray 10 onto the light-receiving surface of the CCD 51; (5) a motor 32 for moving the lens 40 in the optical-axis direction; and (6) an excitation-light cut filter 46 with bands set such that florescence is transmitted but excitation light is not transmitted, the excitation-light cut filter being interposed between the CCD 51 and the lens 40.

The main body 25 of the black box 20 is provided on both side surfaces of the interior wall thereof with 7 rails 21a, 21b, . . . , 21g for holding the sample tray 10, the 7 rails each having a different distance from the lens 40. The rear surface of the interior wall corresponding to the rails 21a to 21g is provided with sensors 22a, 22b, . . . , 22g for detecting whether or not the sample tray 10 is disposed on the rails 21a to 21g. More specifically , the sensor 22a detects whether or not the sample tray 10 is placed on the rail 21a and the sensor 22b detects whether or not the sample tray 10 is placed on the rail 21b. Similarly, the sensor 22c corresponds to the rail 21c, the sensor 22d to the rail 21d, the sensor 22e to the rail 21e, the sensor 22f to the rail 21f, and the sensor 22g to the rail 21g.

The CCD 51 is provided to penetrate the top surface of the interior wall of the black box main body 25, the lens 40 for projecting the image of the gel 11 onto the CCD 51 being moved by stages such that the stopped position (lens position) in the optical-axis direction X is at 41a, 41b, . . . , 41g in accordance with the rail 21a, 21b, . . . , 21g on which the sample tray 10 is placed. More specifically, the lens position 41a is a position suitable for projecting the image of the gel 11 on the sample tray 10 onto the CCD 51 when the sample tray 10 is placed on the rail 21a. The lens position 41b is a position suitable for projecting the image of the gel 11 on the sample tray 10 onto the CCD 51 when the sample tray 10 is place don the rail 21b. Likewise, the lens position 41c corresponds to the rail 21c, the lens position 41d to the rail 21d, the lens position 41e to the rail 21e, the lens position 41f to the rail 21f, and the lens position 41g to the rail 21g. Note that the illustration of 41d to 41f has been omitted, and the markings 10a on the sample tray 10, indicating a plurality of ranges different in size, correspond to the readable ranges of the CCD 51 in accordance with distances from the CCD 51 when the sample tray 10 is placed on each of the rails 21a, 21b, . . . , 21g, respectively.

The movable lens 40 is moved to each of the aforementioned lens positions 41a to 41g by a stepping motor 32 provided inside the black box 20. Input pulse numbers D1, D2, D3, D4, D5, D6, D7 to the steeping motor 32, respectively corresponding to the lens positions 41a, 41b, . . . , 41g, are previously caused to correspond to the rails 21a to 21g and are stored as a reference table in a storage section 33 provided inside the black box 20.

The interior of the black box 20 is further provided with focus control means 31 for receiving a result of detection, indicating any of the rails 22a to 22g that the sample tray 10 is placed on, from one of the sensors 22a to 22g, also calculating the pulse number corresponding to the detection result by referring to the reference table stored in the storage section 33, and inputting the calculated pulse number to the stepping motor 32.

The outline operation of the image information reader 100 constructed as described above will hereinafter be described.

The gel 11 distributing specific organism-originated materials labeled with a fluorescent dye is first placed within a predetermined range on the sample tray 10, by using the markings 10a as a standard. Then, the sample tray 10 with the gel 11 placed thereon is placed on one of the rails 21a to 22g of the image information reader 100 which is appropriate to the markings 10a in a range holding the gel 11. The lens 40 has been stopped at a predetermined initial position. However, with placement of the sample tray 10, the sensor 22d, which corresponds to the rail on which the sample tray 10 was placed among the sensors 22a to 22g disposed within the black box 20 (e.g., the rail 21d in the fourth row), detects that the sample tray 10 has been placed and sends a detection signal to the focus control means 31. At this time, there is no possibility that the other sensors 22a to 22c and 22c to 22g will output detection signals, because the sample tray 10 is not present on the corresponding rails 21a to 21c and 21e to 21g.

The focus control means 31 receives the detection signal, recognizes that the detection signal was output from the sensor 22d, obtains the pulse number D4 corresponding to the sensor 22d by referring to the reference table, and inputs the pulse number D4 to the stepping motor 32. Based on the pulse number input from the focus control means 31, the stepping motor 32 moves the lens 40 from the initial position to the lens position 41d.

Here, the lens position 41d has previously been set as a position suitable for projecting the image of the gel 11 on the sample tray 10 onto the CCD 51 when the sample tray 10 is placed on the rail 21d of the fourth row. Therefore, the CCD 51 is in a position for suitably receiving an image of florescence that is emitted from the gel 11 on the sample tray 10 disposed on the rail 21d of the fourth row.

After the door of the black box 20 has been closed to shield light from the interior thereof, the gel 11 on the sample tray 10 is irradiated with the excitation light emitted from the LEDs 45. The gel 11 irradiated with the excitation light emits florescence, because the fluorescent dye labeling specific organism-originated materials distributed inside the gel 11 is excited. The florescence emitted from the gel 11 is projected as the distributed image of the florescence on the gel 11 onto the light-receiving surface of the CCD 51 through the lens 40 and the excitation light cut filter 46.

Here, the sample tray 10 has been coated with Platinum Stone 10c including, as a black pigment, Silky Black whose content of a fluorescent dye is less, compared with a conventional black Alumite process. Therefore, the florescence that is emitted from the sample tray 10 itself can be reduced to an extremely low level.

On the other hand, part of the excitation light emitted to the gel 11 is reflected at the surfaces of the gel 11, the sample tray 10 or the like and travels in the direction of the CCD 51. However, the excitation light cut filter 46 provided in front of the light-receiving surface of the CCD 51 prevents passage of excitation light and therefore there is no possibility that excitation light will be incident on the light-receiving surface of the CCD 51.

The CCD 51 photoelectrically detects the image of the fluorescence emitted from the gel 11 and outputs an obtained signal to an external image processor, an external image display or the like.

If a sequence of image information reading operations described above ends, the door of the black box 20 is opened and the operator pulls out the sample tray 10 from the interior of the image information reader 100. Then, the placed gel 11 is removed from the taken sample tray 10. Thereafter, the sample tray 10 is rinsed with water or predetermined chemicals. Here, since the sample tray 10 is coated on the surface thereof with Platinum Stone 10c, the fluorescent dye, the organism-originated materials, the gel or the like adhering to the placing surface can easily be rinsed out. Thus, the sample tray 10 is easier to handle than the conventional tray processed with a black Alumite and can be used repeatedly.

Note that the sample tray 10 of the preferred embodiment is provided with a plurality of markings indicating a plurality of sample-placing ranges different in size, because the sample tray 10 has been applied to the image information reader 100 having sample-tray disposing positions of multiple stages. Therefore, the present invention is not limited to this embodiment. For instance, in the case of a sample tray to be used in an image information reader whose readable range is always constant, the sample tray may be provided with only markings indicating a single sample-placing range or with no markings.

What is claimed is:

1. A method of fabricating a sample tray on which a sample distributing specific organism-originated materials labeled with a fluorescent dye is placed, said sample tray being used in an image information reader which is equipped with an excitation light source for emitting excitation light and a photoelectric reading mechanism which photoelectrically reads out fluorescence emitted from said fluorescent dye by said excitation light as a distributed image of said organism-originated materials in said sample, wherein said image information reader employs said excitation light source, said sample tray, said sample, and said photoelectric reading mechanism with an external light shield, said method comprising:

coating at least a surface on which said sample is placed with fluororesin; and forming one of depressed and projected markings, which represent a readable range of said photoelectric reading mechanism, on said surface on which said sample is placed.

2. The method as set forth in claim 1, wherein said fluororesin is a hybrid resin consisting of polytetrafluoroethylene (PTFE) and tetrafluoroethylene-perfluoroalkyl-vinylether copolymer (PFA).

3. A sample tray on which a sample distributing specific organism-originated materials labeled with a fluorescent dye is placed, said sample tray being used in an image information reader, said image information reader including an excitation light source for emitting excitation light and a photoelectric reading mechanism which photoelectrically reads out fluorescence emitted from said fluorescent dye excited by said excitation light as a distributed image of said organism-originated materials in said sample, wherein said image information reader employs said excitation light source, said sample tray, said sample, and said photoelectric reading mechanism with an external light shield, and wherein said sample tray is coated with fluororesin at least on a surface on which said sample is placed such that said sample can be washed away from the fluororesin-coated surface by rinsing.

4. The sample tray as set forth in claim 3, wherein one of depressed and projected markings representing a readable range of said photoelectric reading mechanism are formed in said surface on which said sample is placed.

5. The sample tray as set forth in claim 4, wherein said fluororesin is a hybrid resin consisting of polytetrafluoroethylene (PTFE) and tetrafluoroethylene-perfluoroalkyl-vinylether copolymer (PFA).

6. The sample tray as set forth in claim 3, wherein said fluororesin is a hybrid resin consisting of polytetrafluoroethylene (PTFE) and tetrafluoroethylene-perfluoroalkyl-vinylether copolymer (PFA).

* * * * *